(12) United States Patent
Martin et al.

(10) Patent No.: US 6,403,059 B1
(45) Date of Patent: Jun. 11, 2002

(54) METHODS OF MAKING DENTIFRICE COMPOSITIONS AND PRODUCTS THEREOF

(75) Inventors: Michel J. Martin, Plainsboro, NJ (US); Patrick D. McGill, Darlington, MD (US); Donald M. Gury, Baltimore, MD (US); Yung-Hui Huang; Minas R. Apelian, both of Bel Air, MD (US)

(73) Assignee: J. M. Huber Corporation, Edison, NJ (US)

( * ) Notice: Subject to any disclaimer, the term of this patent is extended or adjusted under 35 U.S.C. 154(b) by 0 days.

(21) Appl. No.: 09/641,639

(22) Filed: Aug. 18, 2000

(51) Int. Cl.$^7$ ............................ A61K 7/16; B24C 1/00; C01B 33/16
(52) U.S. Cl. ........................... 424/49; 51/308; 423/335; 423/338; 423/339
(58) Field of Search ...................... 424/49–58

(56) References Cited

U.S. PATENT DOCUMENTS

| | | | |
|---|---|---|---|
| 3,506,757 A | 4/1970 | Salzmann | 424/52 |
| 3,652,215 A | * 3/1972 | Abouthoul et al. | 23/182 |
| 3,709,664 A | * 1/1973 | Krekler et al. | 23/285 |
| 3,934,000 A | 1/1976 | Barth | 424/49 |
| 4,026,721 A | * 5/1977 | Kurrle | 106/288 |
| 4,069,310 A | * 1/1978 | Harrison | 424/49 |
| RE29,634 E | 5/1978 | Roberts et al. | 424/57 |
| 4,495,167 A | 1/1985 | Nauroth et al. | 423/339 |
| 5,184,434 A | * 2/1993 | Hollinger et al. | 51/317 |
| 5,215,733 A | * 6/1993 | Potter | 423/338 |
| 5,236,696 A | * 8/1993 | Catiis et al. | 424/49 |
| 5,310,543 A | 5/1994 | Dawson | 424/49 |
| 5,328,682 A | * 7/1994 | Pullen et al. | 424/49 |
| 5,603,920 A | 2/1997 | Rice | 424/49 |
| 5,651,958 A | 7/1997 | Rice | 424/49 |
| 5,658,553 A | 8/1997 | Rice | 424/49 |
| 5,676,932 A | 10/1997 | Wason et al. | 424/49 |
| 5,705,137 A | 1/1998 | Goerl et al. | 423/335 |
| 5,891,421 A | 4/1999 | McGill et al. | 424/49 |
| 5,989,524 A | 11/1999 | Dromard et al. | 424/49 |
| 6,267,812 B1 | 7/2001 | Lefer et al. | 106/487 |

FOREIGN PATENT DOCUMENTS

| | | |
|---|---|---|
| EP | 0 785 169 | 7/1997 |
| WO | WO 96/06593 | 3/1996 |
| WO | WO 97/46485 | 12/1997 |
| WO | WO 00/02814 | 1/2000 |

* cited by examiner

*Primary Examiner*—Shep K. Rose
(74) *Attorney, Agent, or Firm*—Carlos Nieves; David Mitchell Goodrich

(57) ABSTRACT

Methods of making dentifrice compositions including, as a raw material ingredient thereof, abrasive compositions comprised of water-insoluble abrasive polishing agents suspended in a liquid medium in combination with humectant, and the unique dentifrice compositions made in this manner.

25 Claims, 1 Drawing Sheet

METHODS OF MAKING DENTIFRICE COMPOSITIONS AND PRODUCTS THEREOF

BACKGROUND OF THE INVENTION

1. Field of the Invention

This invention relates to methods of making dentifrice compositions and the resulting products.

2. Description of the Related Art

Conventional dentifrice compositions typically include an abrasive substance in order to remove various deposits, including pellicle film, from the surface of teeth. Pellicle film is tightly adherent and often contains brown or yellow pigments which impart an unsightly appearance to the teeth. While cleaning is important, the abrasive should not be so aggressive so as to damage the teeth. Ideally, an effective dentifrice abrasive material maximizes pellicle film removal while causing minimal abrasion and damage to the hard tooth tissues. Consequently, among other things, the performance of the dentifrice is highly sensitive to the abrasive polishing agent ingredient. Conventionally, the abrasive polishing material has been introduced in flowable dry powder form to dentifrice compositions, or via re-dispersions of flowable dry powder forms of the polishing agent prepared before or at the time of formulating the dentifrice.

A number of water insoluble, abrasive polishing agents have been used or described for dentifrice compositions. These abrasive polishing agents include natural and synthetic abrasive particulate materials. The generally known synthetic abrasive polishing agents include amorphous precipitated silicas and silica gels and precipitated calcium carbonate (PCC). Other abrasive polishing agents for dentifrices have included chalk, magnesium carbonate, dicalcium phosphate and its dihydrate forms, calcium pyrophosphate, zirconium silicate, potassium metaphosphate, magnesium orthophosphate, tricalcium phosphate, and the like.

Synthetically-produced precipitated silicas, in particular, have been used as abrasive components in dentifrice formulations due to their cleaning ability, relative safeness, and compatibility with typical dentifrice ingredients, such as humectants, thickening agents, flavoring agents, anti-caries agents, and so forth. As known, synthetic precipitated silicas generally are produced by the de-stabilization and precipitation of amorphous silica from soluble alkaline silicate by the addition of a mineral acid and/or acid gases under conditions in which primary particles initially formed tend to associate with each other to form a plurality of agglomerates (i.e., discrete clusters of primary particles), but without aggregation into a three-dimensional gel structure. The resulting precipitate is separated from the aqueous fraction of the reaction mixture by filtering, washing, and drying procedures, and then the dried product is mechanically comminuted in order to provide a suitable particle size and size distribution.

The silica drying procedures are conventionally accomplished using spray drying, nozzle drying (e.g., tower or fountain), flash drying, rotary wheel drying, oven/fluid bed drying, and the like, which often require considerable expenditures for equipment and operating costs. A similar issue is associated with other synthetically derived polishing agents, such as PCC.

Additionally, conventional abrasive polishing agents destined for dentifrice formulations have required comminution in order to reduce the particle size of the dewatered precipitated silica product down to a size that does not feel gritty in the mouth of a dentifrice user, while, on the other hand, not being so small as to lack sufficient polishing action. That is, in conventional practice, the average particle size of the silica in the reactor formed by acidulation of a metal silicate is too large for dentifrice applications and the like. To comminute dry silica particulates, grinding and milling equipment have been used, such as a hammer or a pendulum mill used in one or multiple passes, and fine grinding has been performed, for example, by fluid energy or air-jet mill. These additional dry comminution operations entail added cost and process time. Moreover, conventional dry grinding and milling equipment and methods tends to introduce impurities into the silica which can diminish the brightness, i.e., cause "graying", of the formulation which ultimately incorporates the ground dry silica.

U.S. Pat. No. 3,506,757 to Salzmann describes liquid dentifrices comprising particulate abrasive materials, stably suspended in an aqueous liquid vehicle with the aid of a polysaccharide gum as suspending agent. Similarly, PCT published application no. WO 97/46485 describes silica having a median particle size generally around 12 to 30 µm provided in the form of a suspension, which can be stabilized using a hydrocolloid, particularly naming polysaccharides such as xanthan gum, guar gum, and water-soluble cellulose ethers. U.S. Pat. No. 5,310,543 describes liquid dentifrices containing particulate siliceous abrasive cleaning agents stably suspended in a liquid medium with the aid of a polysaccharide gum and using a liquid medium specified as being substantially free from polyol-type humectants in order to obtain satisfactory rheological properties.

Among other things, dentifrice compositions containing appropriately sized abrasive particles would be desirable that could be prepared as part of a continuous process flow and without the need for costly drying and dry milling/comminuting procedures being done on the abrasive component of the dentifrice.

SUMMARY OF THE INVENTION

The above and other objectives, advantages and benefits are achieved by the present invention which is directed to dentifrice compositions made with an abrasive composition ingredient comprised of water-insoluble abrasive polishing agents suspended in a liquid medium based on humectant. The resulting dentifrice compositions have unique attributes, such as enhanced TAPPI brightness imparted to the abrasive component as processed for incorporation into the dentifrice.

In one embodiment, the invention concerns a method for making dentifrice compositions by a continuous, integrated process without need for performing dewatering procedures on the ingredients of the dentifrice before dentifrice formulating. In particular, the abrasive component used as a raw material in making the dentifrice according to this invention is conveniently and cost-effectively provided as a stable, pumpable slurry of silica, never dried, by dispersing filtered silica cake obtained directly from the precipitation reactor in a humectant. In particular, capital and energy costs are saved by eliminating drying-dewatering operations in the processing of the silica abrasive component used in making a dentifrice composition according to this invention. Further, the comminution requirements for the abrasive particle content of the inventive dentifrices are reduced, if not completely eliminated in some cases, by the effective performance of comminution concurrent with synthesis of the abrasive material to be used in the dentifrice in a common reactor system in the practice of this invention. The water-insoluble abrasive particulate product of the reaction is provided with the requisite particle size suited for oral cleaning compositions to eliminate the need for drying and comminuting dry silica solids after filtration. While not desiring to be bound to any particular theory at this time, it is postulated that the Theological properties of the abrasive compositions used in making dentifrices according to this invention are superior, at least in part, due the avoidance of agglomeration of particles otherwise incurred by the silica particles during conventional silica particle drying procedures. By contrast, the dentifrice compositions made according to this invention contain silica particles that retain or essentially retain the original structure and chemistry of the reactor silica and avoid changes in surface hydroxyl group type and density. In this regard, the undried abrasive particles used in dentifrices made according to this invention show improved TAPPI brightness values as compared to abrasive particles derived from processing involving abrasive particle drying and dry comminuation. "Drying" of the silica particles, for purposes herein, means silica particles have been dehydrated to an extent that a generally dry flowable powder results as the water content is reduced below about 10 wt %. Thus, "dried" or "dry" abrasive particles have been subjected to such drying, as defined above. Also, "dry comminution", means milling or other mechanical attrition performed on dried abrasive particles. The abrasive particles used in the dentifrices made according to this invention are not dried nor dry comminuted. Also, the humectant used as a carrier to deliver the abrasive particle ingredient to a dentifrice formulation under preparation can be applied to the humectant requirements of the dentifrice per se.

DETAILED DESCRIPTION OF THE PREFERRED EMBODIMENT(S)

The dentifrice compositions made according to this invention use abrasive combinations that are highly stable portable, storable, ready-to-use abrasive suspensions or slurries that can be readily formulated on demand with other ingredients to prepare oral cleaning compositions having a high cleaning efficacy without causing undue abrasion on tooth tissues. The methods of making dentifrice compositions according to this invention are described in more detail below.

Figure 1:
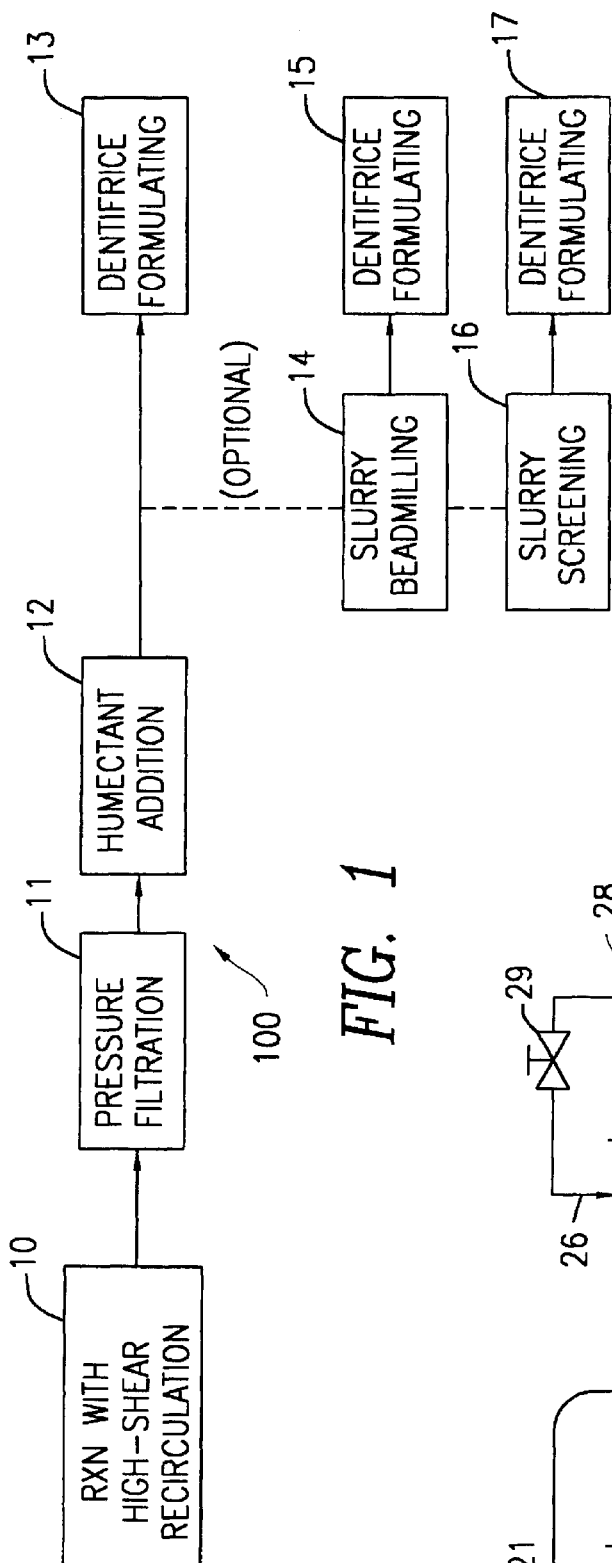
FIG. 1 is a process flow chart of a method scheme for producing a dentifrice composition according to this invention.

Referring to FIG. 1, a generalized processing scheme 100 is illustrated for making a dentifrice composition according to this invention.

In the first step of the processing scheme 100, an acidulation reaction is performed to precipitate silica. The initial acidulation reaction is performed in a reaction system 10 equipped with suitable heating equipment. In general, the precipitated silicas made in step 10 may be prepared by a fresh water, or electrolyte solution, acidulation process wherein silica is precipitated by reaction of an alkali metal silicate and a mineral acid in aqueous solution. In the fresh water process, no electrolyte such as alum, $Na_2SO_4$, or NaCl, is present during the acidulation reaction.

Figure 2:
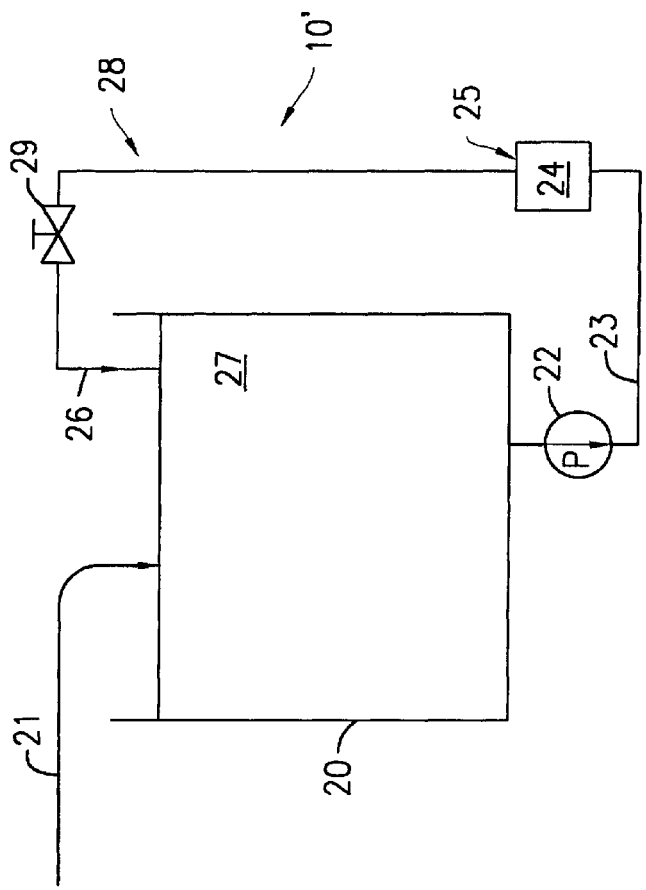
FIG. 2 is a schematic of a reactor system scheme used in the production of an abrasive composition component used in the making of a dentifrice composition according to this invention.

As shown in more detail in FIG. 2, a reactor system 10' is shown used to implement step 10 in FIG. 1. As illustrated, a portion of the sodium silicate solution 21 is charged to a reactor container or chamber 20 including agitator means (not shown) to provide agitation to the container contents 27. Preferably, about 0% to 30% of the total stoichiometric amount of sodium silicate solution is placed in the reactor container 20 to serve as initiating nuclei for the silica. The aqueous solution of sodium silicate in the container 20 is then preheated to a temperature in the range of about 60 to 100° C., more preferably about 80 to 95° C. Prior to introduction into the reactor container 20, the remaining sodium silicate is preferably preheated to about 70 to 95° C. An acid solution is preferably preheated to about 30 to 35° C.

Although sodium silicate is illustrated, it will be understood that any suitable alkali metal silicate could be used. The term "alkali metal silicate" includes all the conventional forms of alkali silicates, as for example, metal silicates, disilicates and the like. Water soluble potassium silicates and sodium silicates are particularly advantageous with the latter being preferred. It should be taken into consideration that the mole ratio of the alkali silicate, i.e., the ratio of silica to alkali metal, contributes, depending on other reaction parameters, to the average pore size of the silica products. In general, acceptable silica products of this invention can be made with silicate molar ratios ($SiO_2$:$Na_2O$) ranging from about 1.0 to 3.5 and preferably from about 2.4 to about 3.4. The alkali silicate solution supplied to the reactor vessel 20 during various processing steps in the inventive method, as described elsewhere herein, generally can contain between about 8 to 35%, and more preferably between about 8.0% and 15.0%, by weight alkali metal silicate based on the total weight of the alkali metal silicate solution. In order to reduce the alkali silicate concentration of a source solution of alkali silicate to the above-indicated desired range, dilution water can be added to a source solution of alkali silicate before the silicate solution is fed into the reactor, or, alternatively, the dilution water can be combined in situ with the source solution of alkali silicate in the reactor 20 with agitation-mixing to formulate the desired concentration of silicate in the alkali metal silicate solution.

The acid, or acidulating agent, can be a Lewis acid or Brönsted acid, and preferably is a strong mineral acid such as sulfuric acid, hydrochloric acid, nitric acid, phosphoric acid, and so forth, and more preferably sulfuric acid, added as a dilute solution thereof (e.g., at a concentration of between about 6 to 35 wt %, more typically about 9.0 to 15.0 wt %).

As shown in FIG. 2, the reactor system 10' also has a recirculation loop 28 including a pump 22, e.g. a centrifugal pump, and a manual valve 29 for control of flow and flow rate through the recirculation loop 28. The pump 22, when activated, and when the valve 29 is opened, will continuously pump a portion of the reactor contents 27 via line 23 to an in-line high shear mixing means 24, e.g., a rotor/stator mixer or Lightnin mixer, which imparts high shear to the reactor contents flowing through it. As a consequence, the in-line mixer 24 effectively serves to reduce the particle size of the suspended silica solids in an aqueous environment. After the high shear treatment in the in-line mixer 24, the conditioned silica suspension is fed through line 26 and re-introduced back in the reactor 20 where it rejoins the reaction mixture 27. The acid feed 25 preferably is introduced at the in-liner mixer 24, although, alternatively, the acid could be introduced directly into the reactor container 20. The sodium silicate solution can be charged directly into the reactor container 20, or at the in-line mixer 24 or both.

Returning now to the general discussion of the process flow, once the reactor solution 27 and remaining reactants have reached the desired temperatures, the manual valve 29 on the recirculation loop 28 is set to an open position. The line-mixer 24 is activated. Then, simultaneous addition of the remaining sodium silicate solution and acid is commenced. Preferably, the acid is introduced at the in-line mixer 24. The sodium silicate solution and acid are metered into the reactor over an addition time of about 30 to 90 minutes. Rates of addition of the reactants depend upon the mol. ratio, addition time and concentration of the silicate and the concentration of the acid. Generally, 2 mol. sodium is neutralized with one mol. sulfuric acid.

At the end of this co-addition period, most of the silica has precipitated and the sodium silicate addition is stopped. Addition of the acid is continued until the reactor slurry reaches the desired pH. Once the slurry pH reaches about 7.0, it is preferable to reduce the acid flow rate until the slurry pH approaches the target pH, at which point the acid flow can be stopped and manual adjustment used to reach the target slurry pH. The preferred slurry pH is approximately 4.0 to 7.0, more preferably between 4.0 to 5.0, and most preferably 4.6±0.1. At this juncture, the silica has precipitated to provide a mixture of the precipitated silica and the reaction liquor. Once the desired slurry pH is reached, digestion begins and the reaction temperature is raised to approximately 85–99° C., and preferably 91 to 97° C., and digestion is continued at the elevated temperature for approximately 5 to 60 minutes, and preferably for approximately 10 minutes. Acid is added during the digestion step to the extent necessary to maintain a constant pH.

One important aspect of the inventive process scheme resides in the use of the high shear in-line mixer 24 to condition the reaction mass and silica particles therein during at least one or more of the above-described precipitation, acid addition and digestion steps. In one preferred embodiment, the in-line mixer is applied to slurry run through the recirculation loop from the time the manual valve 29 is opened and co-addition of the silicate solution and acid initiated until the digestion is complete. Alternatively, the in-line mixer 24 is applied to the slurry being run through the recirculation loop 28 for only a portion of the reaction time. However, in keeping with an objective of this invention of reducing silica particles without the need for drying and dry milling procedures, the amount of shear applied to the reactor slurry contents should be sufficient to reduce the median particle size (MPS) to between about 1 to about 30 microns ($\mu$m), preferably between about 1 and about 25 microns, and more preferably between about 3 and about 10 microns.

To achieve the product particle size desired at the reactor stage of the process, the present invention generally employs a recirculation rate of approximately 8 vol. % to 22 vol. % per minute of the volume of the contents of the reaction container 20 through the recirculation loop 28. The amount of shear also can be expressed in terms of the number of times the entire reactor contents (in liters (L)) are recirculated during the reaction time (in minutes), including through precipitation, digestion and the intervening steps. For this invention, the minimum shear rate is 3.0 and preferably is greater than 4.5, and more preferably greater than 9.0. For example, a 160 L/min recirculation flow for 60 minutes in a 1000 L reactor yields a shear rate, as defined herein, of 9.6.

The in-line mixer 24 employed to impart the high shear to the recirculation flow 28 during the reaction preferably is a rotor/stator type in-line mixer. Examples of useful rotor/stator mixers include Silverson in-line mixers, such as Silverson Model 450LS, manufactured by Silverson Machines, Inc.; or those commercially available from IKA-Works Inc., Wilmington, N.C. 28405, and from Charles Ross and Son Company, Hauppage, N.Y. 11788, including Models ME-410/420X, and 450X.

The basic construction of an in-line rotor/stator type high shear mixer, by itself, which is usable in the practice of this invention is not new per se. It generally includes a shrouded turbine consisting of a rotor and a stator, where the rotor is put in high speed rotation around a shaft while a stationary stator circumferentially surrounds the rotor. The high speed rotation of the rotor blades creates suction which causes the slurry to be treated to be sucked into an entry area of the rotor/stator assembly. From there, the slurry passes through rotor slots and is driven by centrifugal forces into a gap between the stator and ends of the rotor blades where the slurry is subjected to high radial flow shear in the gap. The slurry is then forced through stator slots under intense hydraulic shear to an outlet area where the sheared slurry is piped out for further processing. Fresh slurry is continually drawn into the rotor/stator as sheared slurry departs. In this way, the reactor contents have high shearing forces applied to the recirculation flow 28.

After the digestion step is completed in the reactor system 10' used to implement step 1 in FIG. 1, and any subsequent pH adjustment conducted, the reaction batch is dropped. Namely, the reaction mass is filtered and washed at step 11 (FIG. 1). The filter preferably is a pressure filter, such as a plate and frame filter, filter press or a pressure leaf filter. The reaction mass is filtered and washed with water to reduce the $Na_2SO_4$ level to less than 5%, and preferably less than 2%, by weight (e.g., 0.5 to 1.5%). The resulting wet cake contains about 50 wt % solids content, the balance is essentially all water. The pH of the washed filter cake can be adjusted, if necessary.

In step 12 (FIG. 1), the washed wet cake of step 12 is fluidized with humectant. A humectant, and especially a polyol type humectant, is mixed with the wet filter cake with mixing to provide a suspension or slurry of abrasive particles containing the humectant. Preferably, the mixing is done in a high shear mixer, such as by adding the wet cake into a mixer vessel containing the specified amount of humectant and then mixing the contents until slurry has a +325 mesh residue level of less than 1.5% (based on dry silica weight). Examples of useful mixers in this regard are a Motoregler Dispermat CV high shear mixer, and a Hockmeyer Lab 2 type disperser from Hockmeyer Equipment Company.

It has been discovered that the addition of a relatively small amount of polyol humectant to the wet cake with sufficient mixing to fluidize same yields an abrasive slurry or suspension that is rheologically stable and adequately settling-resistant to avoid the need for extraneous stabilizing agents. Additionally, the polyol humectant treated and fluidized wet cake also does not experience significant re-agglomeration of the silica into larger particle sizes.

To accomplish this, the humectant is added in an amount of about 3 to about 80 wt %, preferably about 5 to about 60 wt %, and more preferably about 20 to about 50 wt %, and can be less than about 30 wt % (e.g. 3 to <30 wt %), based on the wet filter cake weight. If the amount of humectant added to the filtered wet cake is too low, the viscosity of the cake remains too high to permit its fluidization into a slurry form, while, on the other hand, if the amount of humectant is too high, the fluidized slurry will tend to require large amounts of preservatives to maintain control of bio-burden with a concomitant increase in material costs and would contain more humectant than usable in some toothpaste formulations. The humectant preferably is a polyol, such as glycerin, sorbitol, polyethylene glycol, polypropylene glycol, hydrogenated starch hydrolyzate, xylitol, lactitol, and hydrogenated corn syrup, used singly or as mixtures thereof. Glycerin and sorbitol are preferred, as used individually or in combinations. Glycerin is readily obtainable in 99.5 wt % solutions, while sorbitol is often commercially available as a 70 wt % solids aqueous solution. Functionally, the term humectant is customarily understood to refer to a compound which facilitates and ensures moisture retention by compositions incorporating same so as to prevent drying out of the composition upon its exposure(s) to air.

The liquid medium into which the silica wet cake is fluidized will be constituted by both the water or aqueous portion of the filtered wet cake and the humectant additive. As noted above, the humectant itself can be introduced with relatively low water content (e.g., about 30 wt % or less in the case of commercially available 70 wt % solids sorbitol solutions usage and less than about 0.5 wt % for commercially available glycerine usage). However, it will be appreciated that the water retained in the filter cake itself contributes to the fluidizing fluid, as a whole, which adds aqueous character to the overall liquid medium into which the silica particles are suspended.

The resulting abrasive slurry made according to this invention by step 12 in FIG. 1 has a viscosity of ranging from about 100 cP to 700,000 cP, as measured at 25° C. measured on a Brookfield ½ RVDV II Viscometer with a T-F spindle, rpm=5.0 on a Helipath stand, and a solids settling rate of less than 30 wt % after three weeks storage at about 25° C.

The discovery that the addition of amounts of polyol humectant of about 3 wt % to 80 wt % to fine precipitated silica suspensions can yield rheologicaaly stable and settling-resistant abrasive suspensions, which can be used per se or used as additives in further compositions, is thought surprising. Thus, the abrasive composition provided at this stage of processing is stable and particle sized appropriately so as to be portable, storable and used on demand as a ready-to-use multi-component additive for dentifrice compositions. That is, the abrasive suspension product of step 12 is then used in the formulation of a dentifrice as indicated in step 13 of FIG. 1. The abrasive particles are dispersed and distributed substantially uniformly throughout the inventive slurry composition.

The experimental studies reported herein also indicated that the added presence of polysaccharide binder, such as sodium carboxymethylcellulose (CMC), in the abrasive suspension having the small amount of humectant, had a deleterious effect insofar as the settling properties of the slurry. Polysaccharide binders include water-soluble cellulose ethers, guar gum, and xanthan gum, and so forth, and these binder materials are not needed to rheologicaaly stabilize and provide adequate viscosity build up property in the abrasive compositions of the present invention.

The resulting abrasive suspension comprises about 10 to about 60 weight percent of abrasive particles, from about 3 to about 80 weight percent of humectant, and from about 5 to about 50 weight percent water (preferably 5 to 30 weight percent water). Preferably, no polysaccharide binder is present in the inventive abrasive compositions, or only miniscule amounts at most, viz., less than 0.20 wt % polysaccharide and more preferably less than 0.05 wt % polysaccharide is present, if at all (i.e., 0 wt % polysaccharide is more preferred), in the abrasive composition. When the abrasive composition is ultimately combined with other requisite materials, e.g., thickeners, liquid vehicle, fluoride compounds, tartar control agents, and so forth, to form a dentifrice or other oral cleaning composition, it has been observed that the binder then can be combined with the abrasive composition and the other dentifrice ingredients, such as the thickeners and liquid vehicle, without adverse impact on the rheological or silica settling properties.

A preservative, which is an anti-microbial agent (i.e., an anti-bacterial and/or anti-fungal agent), optionally can be added to the fluidized precipitated silica with mixing concurrent with, or immediately after, the fluidization process in step 12 using the polyol humectant. The preservative in this regard can be selected, for example, from the group consisting of sodium benzoate, tetrasodium pyrophosphate, propyl-p-hydroxy-benzoate, and methyl-p-hydroxy-benzoate (methyl paraben). Effective amounts of the preservative seen to adequately prevent bacterial and fungal growth are less than about 0.5 wt % based on the finished toothpaste weight. The preservative, as used in these amounts, does not impact the advantageous rheological properties of the abrasive composition.

An important aspect of this invention is that the aqueous suspension of abrasive particles provided by step 12 can be continuously maintained at a total liquid content of at least 20 wt % up until the additional step of incorporating said aqueous suspension of abrasive particles into a dentifrice composition or other oral cleaning composition without the need to dry the silica or perform dry milling. While not desiring to be bound to any particular theory at this time, it is postulated that drying and dry milling processes impact the agglomeration and surface hydroxyl type and density of the silica particles in unpredictable or even adverse manners. The present invention avoids these impacts of drying and dry milling. The present invention also avoids the adverse effects of conventional dry grinding and milling equipment and methods which can tend to introduce impurities into the silica which can diminish the brightness, i.e., cause "graying", of a formulation which ultimately incorporates the ground dry silica.

Optionally, and referring to FIG. 1, if a very small particle size is desired, or if the high shearing performed in step 10 is truncated for any reason, the invention does permit wet milling, e.g. wet bead milling, of the aqueous suspension of abrasive particles in step 14 after introducing the humectant and before the aqueous suspension of abrasive particles is incorporated into a dentifrice composition. Also, the slurry bead milling in step 14 can be followed by slurry screening in step 16 to remove particle sizes greater than 325 mesh (45 micron), which, in the practice of this invention are consistently below 1.5 wt % in amount. Alternatively, the screening step 16 can be performed in lieu of the beadmilling step to remove particle sizes greater than 325 mesh.

The silicas provided in the above-illustrated abrasive compositions are preferably characterized as synthetic hydrated amorphous silicas, known as silicon dioxides or $SiO_2$. These precipitated silicas can be characterized as very low to medium structure synthetic silicas in accordance with the definitions set forth in J. Soc. Cosmet. Chem., 29, 497–521 (August 1978), and Pigment Handbook: Volume 1, Properties and Economics, 2nd ed., John Wiley & Sons, 1988, p. 139–159.

In addition to the above-described step 10 methodologies of precipitating the synthetic amorphous silicas, the preparation of the silicas is not necessarily limited thereto and it also can be generally accomplished in accordance with the methodologies described, for example, in prior U.S. Pat. Nos. 3,893,840, 3,988,162, 4,067,746, 4,340,583, and 5,225,177, all of which are incorporated herein by reference, as long as such methods are appropriately modified to incorporate the recirculation and high shear treatment used in step 10. As will be appreciated by one skilled in the art, reaction parameters which affect the characteristics of the resultant precipitated silica include: the rate and timing at which the various reactants are added; the levels of concentration of the various reactants; the reaction pH; the reaction temperature; and/or the rate at which any electrolytes are added.

Also, the reactor system 10' (FIG. 2) could be reconfigured in several alternative schemes to the above-described recirculation loop scheme and manner of operation for providing the smaller particle sizes in the reactor slurries. For instance, instead of being introduced at the in-line high shear mixer in the recirculation loop 28, the acid (25) instead can be introduced directly into the reactor vessel 27. The present investigators have observed that the particles sizes of the precipitated solid product in the reactor are relatively smaller, although still within the ranges described herein (i.e., between about 1 to about 30 microns), where the acid is introduced at the in-line shear mixer as shown in FIG. 2 versus being introduced directly into the reaction vessel, all other things equal. Also, the recirculation loop 28 instead could be used with a static line mixer in the recirculation loop 28. Alternatively, instead of using the recirculation loop 28 equipped with a high shear mixer, a high shear turbine reactor agitator could be deployed directly inside the reactor vessel 20 to mix the raw precipitation reaction materials and slurry 27. For that scenario, the raw precipitation reaction materials could introduced close to the high shear reactor agitator, e.g., at the bottom of the reactor. Alernatively, for direct addition to the reactor, the acid can be dispersed through an agitator shaft and out the tip of the agitator blade deployed in the reaction mixture 27 in the reactor vessel 20 to react with remaining sodium silicate and reaction slurry, and this scenario can be used in the reactor system with or without the recirculation loop 28 described above. Also, the raw precipitation reactant materials could be introduced into the reaction slurry in the reactor via a high pressure pump and nozzle arrangement. Also, high shearing action could be applied initially to the raw precipitation reactant materials in a separate small mixing vessel where the high shear is applied through a cowles type mixer, where the reaction mix then overflows into the main reactor vessel using high shear to normal agitation.

The precipitated silicas used in the abrasive compositions of this invention generally have the following properties: 10% Brass Einlehner hardness values in the range between 0.5 and 30, a BET value of 20 to 250 m$^2$/g, linseed oil absorptions between about 40 to about 200 cc/100 g, RDA (Radioactive Dentin Abrasion) values between about 30 to about 200, and PCR (Pellicle Cleaning Ratio) values of 50 to 200. However, it must be borne in mind that an average particle size of 3 to 15 microns for the silica is achieved in the reactor in the present invention by the recirculation loop 28 treatment discussed herein, without the need to include post-reactor drying and dry milling/comminution procedures and related equipment.

Although silicas have been illustrated herein as the abrasive polishing agent component provided in the abrasive compositions being produced by this invention, it will be understood that the principles of the present invention are also considered applicable to suspensions or slurries of other water-insoluble abrasive particles that can be synthesized in a reactor, at least insofar as the stabilizing effect of combining an aqueous suspension of the abrasive particles with less than 80 wt % amount of humectant, and the humectant level can be even less than 30 wt %, without the need for any intervening drying or dry milling steps. Other such water-insoluble particles include, for example, precipitated calcium carbonate (PCC), dicalcium phosphate dihydrate, silica gel and calcium pyrophosphate. Other synthetic abrasive particles, such as PCC, can be synthesized by modifying an otherwise conventional PCC reactor to include use of a recirculation/in-line high shear mixer loop 28 as described herein, to provide a reactor slurry particle size small enough to eliminate the need for post-drying and dry comminuting procedures.

Optionally, in the fluidization step 12 (FIG. 2), different water in-soluble particulate polishing agents, such as precipitated calcium carbonate, dicalcium phosphate dihydrate, calcium pyrophosphate, hydrated alumina, insoluble sodium metaphosphate, insoluble potassium metaphosphate, insoluble magnesium carbonate, zirconium silicate, aluminum silicate, and/or silica gel, and so forth, can be introduced during the precipitated silica slurrying procedure of step 12 to tailor the polishing characteristics of the slurry, if desired.

In any event, the abrasive suspension or slurries obtained from any of steps 12, 14 or 16 indicated in FIG. 1 can then be piped, loaded for transport, or stored, until needed for later usage, in the preparation of the dentifrice or other oral cleaning compositions. In this regard, the aqueous suspension of abrasive particles typically will be combined with at least one of additional water, additional humectant as needed, a binder, a fluoride ion-providing compound, a flavoring agent, a coloring agent, a whitening agent, a preservative, an anti-plaque compound, a foaming agent, and an anti-microbial agent.

Examples of use of these optional dentifrice ingredients are described herein and/or, for example, in Reissue 29,634, U.S. Pat. Nos. 5,676,932, 6,074,629 and 5,658,553, and the patents cited therein, all being incorporated herein by reference. These optional ingredients, if used, can be used at levels that are customarily seen in dentifrice formulations.

The precipitated silica component of the above-described silica suspension product (step 12 product in FIG. 1), when incorporated into dentifrice compositions (step 13, 15 or 17), is present at a level of from about 10% to about 50% by weight, more preferably from about 10% to about 35% by weight, when the dentifrice is a toothpaste. Overall dentifrice or oral cleaning formulations incorporating the abrasive compositions of this invention conveniently can comprise the following possible ingredients and relative amounts thereof (all amounts in wt %):

Dentifrice Formulation:

| Ingredient | Amount |
| --- | --- |
| Liquid Vehicle: | |
| humectant (s) (total) | 5–70 |
| deionized water | 5–70 |
| binder (s) | 0.5–2.0 |
| anticaries agent | 0.1–2.0 |
| chelating agent (s) | 0.4–10 |
| silica thickener* | 3–15 |

-continued

| Ingredient | Amount |
| --- | --- |
| anionic surfactant (s) | 0.5–2.5 |
| abrasive | 10–50 |
| sweetening agent | <1.0 |
| coloring agents | <1.0 |
| flavoring agent | <5.0 |
| preservative | <0.5 |

Useful silica thickeners include, for example, an amorphous precipitated silica such as Zeodent® 165 silica. Other preferred silica thickeners are Zeodent® 163 and Zeofree® 153 silicas, all available from J. M. Huber Corporation, Havre de Grace Md., U.S.A.

EXAMPLES

The following examples are presented to illustrate the invention, but the invention is not to be considered as limited thereto. In the following examples, parts are by weight unless indicated otherwise.

Example 1

In order to assess the rheological and settling attributes of abrasive composition component of the inventive dentifrices made according to the invention versus comparative abrasive compositions derived from dried and dry milled silicas, silicas first were prepared as follows.

Silica Wet Cake Preparation:

Silica Wet Cake 1 (WC1):

24.8 liters (L) of sodium silicate (13.3% $Na_2O$, 2.65 mol. ratio of $SiO_2$:$Na_2O$; specific gravity of 1.123) was added to a 1000 L stainless steel reactor jacketed for steam heating. An A200 Lightnin agitator that had been placed inside the reactor was set at 120 rpm. The reactor system also had been provided with an external recirculation loop including a Labour ASME B73.1 (Sterling Fluid Systems) centrifugal pump, a manual flow rate control valve, and a Silverson 450 LS in-line mixer, with intake to the loop established at the bottom of the vessel, and return established near the top of the vessel, and appropriate piping provided between these components. The reaction medium was preheated to 83° C., and this temperature was maintained for the duration of the reaction. Recirculation was started to achieve a recirculation flow rate of 108 L/min, with the Silverson mixer activated and set at 60 Hz. The manual valve on the recirculation system was set to fully open. Then, simultaneous acid and silicate flow to the reactor system was initiated and continued for a given time period. The dilute sodium silicate, preheated to 83° C., of the same concentration/composition described above was introduced to the reactor vessel at 13.00 liters/min (LPM), while at the same time, a dilute sulfuric acid (11.4 wt %, SG=1.079, 39° C.) was introduced at 3.56 LPM (start acid slowly 1 LPM) at the Silverson mixer. The silicate flow was discontinued after 47 minutes of the co-addition. The acid flow was continued at 3.56 LPM until the batch pH dropped to 7.0. At a batch pH of 7.0, the acid flow was reduced to 1.5 LPM, and the acid addition continued until the pH approached 4.6, at which time the acid flow was close to 4.6 and was then manually adjust to a target of 4.6±0.1 pH. The batch was then digested at 93° C. for 10 minutes, with the pH adjusted back towards 4.6 as needed throughout digestion. After digestion, the pH was manually adjust to 4.6±0.1 pH. The reactor silica median particle size (MPS) was determined for a small sample of the silica removed for this purposes after digestion was completed. The median particle size was 7.76 μm. After digestion was completed, the batch was dropped and then filtered on a plate and frame filter, and then washed to remove most (to <2.0 wt %) of the reaction by-product (sodium sulfate). The batch was filtered using a fill pressure=80 psi, a water pressure=20–25 psi, air blow=80 psi (air blow until water stops coming out of press). Three or four frames of wet cake were collected to be used either for subsequent humectant-fluidization, or spray drying/milling, process routes to be compared.

As will be explained in more detail infra, some of the wet cake product was fluidized using a small amount humectant to represent abrasive suspensions of the invention, while other wet cake was spray dried and dry milled for comparison sake. The spray drying used on the comparison samples involved drying other wetcake made in the manner described above to a target of 7.0% H2O, ±1% using an atomizing spray drying means having an inlet temperature at 480° C. All slurry runs should have similar outlet temperatures. The spray dried samples of comparative silica were then Hammermilled to 8–14 μm.

Silica Wet Cake 2 (WC2):

24.8 L of sodium silicate (13.3% $Na_2O$, 2.65 mol. ratio of $SiO_2$:$Na_2O$; specific gravity of 1.123) and 1.78 kg $Na_2SO_4$ was added to a 1000 L stainless steel reactor jacketed for steam heating. An A200 Lightnin agitator that had been placed inside the reactor was set at 120 rpm. The reactor system used was the same as described in the production of Sample Wet Cake 1. The reaction medium was preheated to 93° C., and this temperature was maintained for the duration of the reaction. Recirculation was started to achieve a recirculation flow rate of 161 L/min, with the Silverson mixer activated and set at 60 Hz. The manual valve on the recirculation system was set to fully open. Then, simultaneous acid and silicate flow to the reactor system was initiated and continued for a given time period. The dilute sodium silicate, preheated to 88° C., of the same concentration/composition described above was introduced to the reactor vessel at 13.00 LPM, while at the same time, a dilute sulfuric acid (11.4 wt %, SG=1.079, 39° C.) was introduced at 4.74 LPM (start acid slowly 1 LPM) at the Silverson mixer. The silicate flow was discontinued after 47 minutes of the co-addition. The acid flow was continued at 4.74 LPM until the batch pH dropped to 7.0. At a batch pH of 7.0, the acid flow was reduced to 1.5 LPM, and the acid addition continued until the pH approached 4.6, at which time the acid flow was close to 4.6 and was then manually adjust to a target of 4.6±0.1 pH. The batch was then digested at 98° C. for 10 minutes, with the pH adjusted back towards 4.6 as needed throughout digestion. After digestion, the pH was manually adjust to 4.6±0.1 pH. The reactor silica MPS was determined for a small sample of the silica removed for this purposes after digestion was completed. The reactor silica MPS was 6.41 μm. After digestion was completed, the batch was dropped and then filtered on a plate and frame filter, and then washed to remove most (to <2.0 wt %) of the reaction by-product (sodium sulfate). The batch was filtered using a fill pressure=80 psi, a water pressure=20–25 psi, air blow=40 psi (air blow until water stops coming out of press). Three or four frames of wet cake were collected to be used either for subsequent humectant-fluidization, or spray drying/milling, process routes to be compared.

Silica Wet Cake 3 (WC3):

The basic procedure used to make Silica wet cake 2 was repeated except that 50.9 L of sodium silicate was initially charged into the reactor, a recirculation flow rate of 116 L/min was used, introduction rate of the sodium silicate solution during the silicate/acid co-addition period was 12.44 LPM, and the batch was dropped. The reactor silica MPS was 8.36 μm.

Silica Wet Cake 4: (WC4)

Silica Wet Cake 4 consists of a 20:80 mixture of Wet cake 2 and Wet cake 1.

The physical properties of the silicas in silica wet cakes 1–4, including the properties of the comparative dried versions thereof, are set forth below in Table 1.

TABLE 1

Silica Slurry Product Physicals

| Silica Wet Cake | WC1 | WC1 (dry) | WC2 | WC2 (dry) | WC3 | WC3 (dry) | WC4 | WC4 (dry) |
|---|---|---|---|---|---|---|---|---|
| % $H_2O$ | 54.64 | 5.7 | 46.7 | 5.9 | 49.7 | 5.6 | 53.05 | 5.2 |
| % 325 Mesh | 1.92 | 0.01 | 1.17 | 0.00 | 4.12 | 0.04 | 1.0 | 0.00 |
| 5% pH | — | 7.72 | — | 6.50 | — | 7.35 | — | 7.49 |
| % $Na_2SO_4$ | — | <0.35 | — | <0.35 | — | <0.35 | — | <0.35 |
| MPS, (μm) | 11 | 7.70 | 6.93 | 6.26 | 10.45 | 9.20 | 8.94 | 7.90 |
| TAPPI Brightness | 98.4 | 96.5 | 97.3 | 96.0 | 97.5 | 95.1 | 97.7 | 96.9 |
| CTAB S.A., $m^2/g$ | — | 46 | — | 32 | — | 47 | — | 43 |
| BET SA., $m^2/g$ | — | 242 | — | 214 | — | 209 | — | 245 |
| Oil Absorption, (cc/100 g) | — | 74 | — | 49 | — | 67 | — | 87 |
| Hg Intrusion - (mL/g) | — | 2.1806 | — | 1.1906 | — | 1.3688 | — | 1.7738 |
| Einlehner Abrasion Dry product, mg | — | 4.86 | — | 8.1 | — | 7.84 | — | 7.64 |
| Einlehner Abrasion Wet cake, mg | 3.51 | — | 12.28 | — | 7.68 | — | 7.28 | — |

*comparison runs in which the wet cake was spray dried and milled as described above in the protocol provided under the Silica Wet Cake 1 heading It is seen from the above data that the TAPPI brightness of wet cakes 1 to 3 is significantly higher (up to 2.4 points) than their spray dried and milled counterparts.

Wet cakes that had not been dried and dry milled were combined with humectant in further studies using the following protocol, and the properties of the resulting abrasive compositions were also assessed and reported below.

Fluidization of Silica Wet Cake:

Slurries 1–5 were prepared from above Silica Wet Cake 3 as follows. For each slurry sample, a specified amount of 70% sorbitol and silica wet cake, indicated in Table 2, was added into a 1200-ml stainless steel beaker. Using a Motor-regler Dispermat CV high shear mixer at 1000 RPM, addition of wet cake to the solution was begun. The wet cake was derived from the above wet cake preparation procedure described for Silica Wet Cake 3. As the viscosity builds, the Dispermat RPM was increased to 6000 RPM maximum. The wet cake product addition continued. Once addition was completed, the Dispermat RPM was maintained at 6000 RPM and the contents dispersed for 10 more minutes.

The viscosity of these fluidized slurries was determined according to the following procedure and are summarized in Table 2 below.

Viscosity Procedure

1. Set up a Brookfield ½ RVDV II Viscometer with a F or B spindle, depending on viscosity, and operated at 5.0 r.p.m., and outfitted with a Helipath stand.
2. Place spindle at top surface of slurry
3. Record viscosity, in centapoise (cP), at 24 seconds.

TABLE 2

| Abrasive Slurry No. | 1 | 2 | 3 | 4 | 5 |
|---|---|---|---|---|---|
| Sorbitol 70%, g | 40 | 80 | 160 | 320 | 640 |
| Silica Wetcake 3, g | 760 | 720 | 640 | 480 | 160 |

TABLE 2-continued

| Abrasive Slurry No. | 1 | 2 | 3 | 4 | 5 |
|---|---|---|---|---|---|
| wt % Sorbitol | 5 | 10 | 20 | 40 | 80 |
| Spindle | F | F | B | B | B |
| Viscosity, cP (@24 sec.) | 914000 | 70000 | 8080 | 1080 | 640 |

Example 2

To investigate the rheological stability of abrasive compositions (i.e., slurries) based on humectant fluidization treatments of the silicas made according to the Silica Wet Cake 1 and Silica Wet Cake 2 preparations as described in Example 1, the following settling studies were conducted. The slurries were prepared using the protocol described above under the heading "Fluidization of the Silica Wetcake", except that Silica Wet Cake 3 was treated for these studies. Comparative runs 3B, 3D, 3F, and 3H were included in which an amount of a polysaccharide binder was also added to the slurry during its preparation.

Silica Slurry Settling Test Protocol:

1. After the fluidized silica sample had been stored at room temperature (25° C.) without agitation for the particular test period (three weeks), the total weight of slurry and jar was measured.
2. The height of the slurry was measured, and the agitator blade was positioned at one-half of the slurry height in the jar.
3. The slurry was agitated at 1000 rpm for 5 minutes.
4. The agitator was removed from jar, the jar was inverted to dump slurry into beaker. The jar was held in an inverted position for 1 minute.
5. The combined weight of slurry remaining in the jar and the jar weight, was measured. The remaining slurry was removed from the jar, the jar was cleaned and the tare weight of the jar was obtained.

6. Then the % weight of the slurry remaining in the jar was calculated based on the starting slurry weight. The results are summarized in Tables 3.

TABLE 3

| Run | 3A | 3B | 3C | 3D | 3E | 3F | 3G | 3H |
|---|---|---|---|---|---|---|---|---|
| Silica wet cake | WC2 | WC2 | WC1 | WC1 | WC2 | WC2 | WC1 | WC1 |
| Silica Wetcake., g | 172.27 | 172.27 | 202.57 | 202.57 | 172.27 | 172.27 | 202.57 | 202.57 |
| Glycerin 99.5%, g | 195.48 | 195.48 | 195.48 | 195.48 | 0 | 0 | 0 | 0 |
| Sorbitol 70%, g | 0 | 0 | 0 | 0 | 195.48 | 195.48 | 195.48 | 195.48 |
| Water added, g | 30.2 | 30.2 | 0 | 0 | 30.2 | 30.2 | 0 | 0 |
| CMC-7MXF*, g | 0 | 1.95 | 0 | 1.95 | 0 | 1.95 | 0 | 1.95 |
| Total Wt., g | 398 | 400 | 398 | 400 | 398 | 400 | 398 | 400 |
| % Settling - 3 weeks | 1.60 | 6.27 | 1.44 | 5.43 | 1.68 | 10.79 | 2.16 | 7.43 |

*CMC-7MXF is carboxymethylcellulose available from Aqualon, division of Hercules Corporation, Wilmington, DE.

The results show that the humectant-fluidized silicas are highly resistant to settling over time.

Example 3

To investigate the interaction and stability of the above-described fluidized silicas with an admixed anti-microbial preservative, the following bioburden study was conducted.

According to the ingredient amounts listed in Table 4, slurries are prepared with varying amounts of sorbitol and sodium benzoate to study biological effects over the aging period. The silica wet cake 1 (WC1) was initially aged for about 1.5 weeks to allow bacteria growth prior to addition of sorbitol or sodium benzoate. Sorbitol and sodium benzoate are placed into a 1200 mL stainless steel beaker and a Dispermat high speed mixer is placed in the beaker. The mixer is set on low speed while the required amount of aged silica wet cake 1 is added. Thereafter, the mixer speed is increased to 6000 rpm and the slurry is mixed for 10 minutes. Each batch is divided into 2 equal parts and transferred into 250 ml sterile jars for 1 week and 3 week testing, respectively. After the designated elapsed time, corresponding samples from each batch are analyzed for total aerobic plate count, mold, yeast and gram negative bacteria according to USP microbiological protocol.

The results of the bio-burden studies are summarized in Table 4 below.

As is seen from the above data, samples treated with sodium benzoate exhibited the most bacterial, mold and yeast extinction, especially those with lower sorbitol levels.

Example 4

Toothpaste formulations were prepared using several of the above-described silicas fluidized with humectant.

For purposes of this invention, a "dentifrice" has the meaning defined in Oral Hygiene Products and Practice, Morton Pader, Consumer Science and Technology Series, Vol. 6, Marcel Dekker, N.Y. 1988, p. 200, which is incorporated herein by reference. Namely, a "dentifrice" is ". . . a substance used with a toothbrush to clean the accessible surfaces of the teeth. Dentifrices are primarily composed of water, detergent, humectant, binder, flavoring agents, and a finely powdered abrasive as the principal ingredient . . . a dentifrice is considered to be an abrasive-containing dosage form for delivering anti-caries agents to the teeth." Dentifrice formulations contain ingredients which must be dissolved prior to incorporation into the dentifrice formulation (e.g. anti-caries agents such as sodium fluoride, sodium phosphates, flavoring agents such as saccharin). In the practice of the present invention, since the inventive abrasive-humectant slurry of step 12 (FIG. 2) contains part or even in some cases, most of the liquid phase needed ultimately for a dentifrice formulation incorporating same, these ingredients can be added to the abrasive-humectant slurry, during or after step 12. Binders are avoided in the inventive polishing slurries due to observations, reported herein, that solid settling is increased in the abrasive slurries where the binder is present in the pre-dentifrice slurry.

TABLE 4

| Silica WC (g) | Sorbitol (g) | Sodium Benzoate (g) | Age Time* (wks) | Aerobic Plate Count CFU/g | Mold CFU/g | Yeast CFU/g | Gram Negative bacteria CFU/g |
|---|---|---|---|---|---|---|---|
| Aged WC1 | 0 | 0 | 0 | 2,800,000 | <10 | <10 | <10 |
| 41.45 | 9.57 | 0 | 1 | 2,200,000 | 7300 | <10 | <10 |
| 41.45 | 9.57 | 0 | 3 | 310,000 | 20,000 | <10 | <10 |
| 41.45 | 38.26 | 0 | 1 | 6100 | 20 | <10 | <10 |
| 41.45 | 38.26 | 0 | 3 | 12,000 | 14,000 | 42,000 | <10 |
| 41.45 | 9.57 | 0.5 | 1 | 570 | <10 | <10 | <10 |
| 41.45 | 9.57 | 0.5 | 3 | 20 | <10 | <10 | <10 |
| 41.45 | 38.26 | 0.5 | 1 | 7900 | <10 | <10 | <10 |
| 41.45 | 38.26 | 0.5 | 3 | 1,500 | <10 | <10 | <10 |

*Time zero = 1.5 week aged wet cake before addition of sorbitol or sodium benzoate To prepare the dentifrices, in the case where the toothpaste formulation contains more than 3 percent water not accounted for by the abrasive-humectant suspension, the following procedure is followed. The humectant (glycerin, sorbitol) amount not included in the abrasive-humectant suspension, sodium carboxymethyl cellulose, polyethylene glycol are mixed together to form a first admixture. The deionized water amount not included in the abrasive-humectant suspension, sodium fluoride, tetrasodium pyrophosphate and sodium saccharin are also mixed together until these ingredients are dissolved to form a second admixture. These two mixtures are combined with stirring. Thereafter, color is added and the combined mixture is stirred with a Lightnin mixer to obtain a "Pre-mix".

The "Pre-mix" is placed in a Ross mixer (Model 130 LDM) and the abrasive-humectant suspension, silica thickener and any required $TiO_2$ are added and mixed without vacuum. A 30 inch vacuum is then drawn and the resultant admixture is stirred for approximately 15 minutes. Lastly, sodium lauryl sulfate and flavor are added and the admixture is stirred for approximately 5 minutes at reduced mixing speed.

In the case where the toothpaste formulation does not contain at least 3 percent water not accounted for by the abrasive-humectant slurry or suspension of this invention, some ingredients must be added to this abrasive slurry or suspension of the invention. Specifically, any remaining formulation water, sodium fluoride, tribasic sodium phosphate, monosodium phosphate, saccharin and color are added to the abrasive-humectant suspension with stirring. Any remaining formulation humectant (e.g., sorbitol, glycerin), CMC (sodium carboxymethyl cellulose), and polyethylene glycol (PEG) are stirred together to form a second admixture. These two admixtures are placed in a Ross mixer and any silica thickener and $TiO_2$ are added and mixed without vacuum. A 30 inch vacuum is then drawn and the resultant admixture is stirred for approximately 15 minutes. Lastly, sodium lauryl sulfate and flavor are added and the admixture is stirred for approximately 5 minutes at reduced mixing speed. The resulting dentifrice composition is sealed in toothpaste tubes and held under appropriate conditions for later testing. The composition had a pH of about 7.

A portion of Silica Wet Cakes 1 to 3, as described above, were fluidized with either glycerin or sorbitol in amounts as described in Table 5A below, and thereafter dentifrices were formulated with these fluidized silica wet cakes as described in Table 5B below. The general protocol for fluidizing the silica wet cakes was the same as that described under the above heading "Fluidization of Silica Wet Cake", except some but not all of the fluidized silica wet cakes were screened through a 325 mesh screen, as indicated in Table 5a. The slurries were screened through a 325 mesh screen to ensure that the +325 mesh residue level was less than 1.5% maximum (based on dry silica weight). To do this, the silica/humectant slurry was poured onto a 325 mesh (45 micron)screen. Slurry was pushed through the screen with a flat object until only the oversize particles remained on the top of the screen.

Properties of these dentifrice formulations are given in Table 5C below.

TABLE 5A

Toothpaste Formula A

| Slurry Component Make-up Abrasive Slurry No. | 6 | 7 | 8 | 9 | 10 | 11 | 12 | 13 | 14 |
|---|---|---|---|---|---|---|---|---|---|
| Sorbitol, 70%, g | 103.6 | 93.5 | 88.2 | — | — | — | — | — | — |
| Glycerin, 99.5%, g | — | — | — | 116 | 116 | 116 | — | — | — |
| WC1 | 414.5 | 13 | — | 414.5 | — | — | — | — | — |
| WC2 | — | — | 352.7 | — | — | 352.7 | — | — | — |
| WC3 | — | 373.8 | — | — | 373.8 | — | — | — | — |
| WC1 (dry & milled) | — | — | — | — | — | — | 20 | — | — |
| WC2 (dry & milled) | — | — | — | — | — | — | — | — | 20 |
| WC3 (dry & milled) | — | — | — | — | — | — | — | 20 | — |
| Total | 518.1 | 467.3 | 440.9 | 530.5 | 489.8 | 468.7 | 20 | 20 | 20 |
| 325 Residue, % | 1.16 | 6.2 | 2.34 | 1.29 | 7.32 | 2.7 | — | — | — |
| Viscosity (cP)** | 2280 | 6640 | 1640 | 1880 | 3840 | 960 | — | — | — |
| Screened | — | yes | yes | — | yes | yes | — | — | — |

*comparison runs in which the wet cake was spray dried and hammer milled as described above using the protocol provided under the Silica Wet Cake 1 heading
**The viscosity values were determined according to the "Viscosity Procedure" described above.

TABLE 5B

Toothpaste Formulation A

| Toothpaste Formula # | 1 | 2 | 3 | 4 | 5 | 6 | 7 | 8 | 9 |
|---|---|---|---|---|---|---|---|---|---|
| Glycerin, 99.5%, g | 11.6 | 11.6 | 11.6 | 0 | 0 | 0 | 11.6 | 11.6 | 11.6 |
| CMC-7MF*, g | 1.4 | 1.4 | 1.4 | 1.4 | 1.4 | 1.4 | 1.4 | 1.4 | 1.4 |
| Sorbitol, 70%, g | 27.9 | 28.91 | 29.44 | 38.257 | 38.257 | 38.257 | 38.257 | 38.257 | 38.257 |
| Deionized water, g | 3.55 | 7.62 | 9.73 | 3.55 | 7.62 | 9.73 | 25 | 25 | 25 |
| Sodium Fluoride, g | 0.243 | 0.243 | 0.243 | 0.243 | 0.243 | 0.243 | 0.243 | 0.243 | 0.243 |
| Sodium Saccharin, g | 0.3 | 0.3 | 0.3 | 0.3 | 0.3 | 0.3 | 0.3 | 0.3 | 0.3 |
| Sodium, Benzoate, g | 0.5 | 0.5 | 0.5 | 0.5 | 0.5 | 0.5 | 0.5 | 0.5 | 0.5 |
| $TiO_2$, g | 0.5 | 0.5 | 0.5 | 0.5 | 0.5 | 0.5 | 0.5 | 0.5 | 0.5 |

TABLE 5B-continued

Toothpaste Formulation A

| Toothpaste Formula # | 1 | 2 | 3 | 4 | 5 | 6 | 7 | 8 | 9 |
|---|---|---|---|---|---|---|---|---|---|
| Abrasive Slurry No. | | | | | | | | | |
| 6, g | 51.81 | — | — | — | — | — | — | — | — |
| 7, g | — | 46.73 | — | — | — | — | — | — | — |
| 8, g | — | — | 44.09 | — | — | — | — | — | — |
| 9, g | — | — | — | 53.05 | — | — | — | — | — |
| 10, g | — | — | — | — | 48.98 | — | — | — | — |
| 11, g | — | — | — | — | — | 46.87 | — | — | — |
| 12, g | — | — | — | — | — | — | 20 | — | — |
| 13, g | — | — | — | — | — | — | — | 20 | — |
| 14, g | — | — | — | — | — | — | — | — | 20 |
| Sodium lauryl sulfate, g | 1.2 | 1.2 | 1.2 | 1.2 | 1.2 | 1.2 | 1.2 | 1.2 | 1.2 |
| Flavor, g | 1 | 1 | 1 | 1 | 1 | 1 | 1 | 1 | 1 |
| Total | 100.00 | 100.00 | 100.00 | 100.00 | 100.00 | 100.00 | 100.00 | 100.00 | 100.00 |

*CMC-7MXF is carboxymethylcellulose available from Aqualon, division of Hercules Corporation, Wilmington, DE.

TABLE 5C

Toothpaste Formulation A Performance Data

| Toothpaste Formula # | 1 | 2 | 3 | 4 | 5 | 6 | 7 | 8 | 9 |
|---|---|---|---|---|---|---|---|---|---|
| Initial Viscosity, cP | 550,000 | 270,000 | 220,000 | 510,000 | 170,000 | 250,000 | 270,000 | 270,000 | 160,000 |
| 1 Wk Viscosity, cP | 700,000 | 300,000 | 280,000 | 620,000 | 320,000 | 300,000 | 360,000 | 300,000 | 210,000 |
| 3 Wk Viscosity, cP | 720,000 | 470,000 | 330,000 | 580,000 | 280,000 | 350,000 | 370,000 | 270,000 | 260,000 |
| 6 Wk Viscosity, cP | 790,000 | 380,000 | 300,000 | 690,000 | 270,000 | 360,000 | 270,000 | 240,000 | 240,000 |
| 25% pH | 6.54 | 6.35 | 6.2 | 6.47 | 6.37 | 6.05 | 6.66 | 6.85 | 6.46 |
| Specific Gravity | 1.3 | 1.298 | 1.296 | 1.304 | 1.296 | 1.292 | 1.295 | 1.308 | 1.283 |
| % F/A 3 Wk 80° F. | 101 | 100 | 100 | 100 | 86 | 95 | 100 | 97 | 95 |
| L value | 91.1 | 90.9 | 90.4 | 90.9 | 89.8 | 90.7 | 90.6 | 89.9 | 89.4 |
| a | −1.3 | −1.8 | −2.1 | −2.1 | −2.2 | −2.1 | −2.1 | −2.1 | −2.1 |
| b | 2.5 | 3.8 | 4.1 | 3.8 | 3.5 | 3.1 | 3.1 | 3.7 | 3.3 |
| RDA | 88 | — | 187 | — | — | — | 107 | — | 197 |

*% Fluoride availability (% F/A) after storage for 3 weeks at 80° F.

It is seen from the above data that the dentifrices made with inventive silica abrasive slurries have several advantages over those made with dry powdered abrasives. Namely, the inventive abrasive slurries provide about 1 point brightness improvement in this dentifrice formulation and they are less abrasive, as compared to their dried and milled counterparts. All dentifrices exhibited good viscosity, fluoride availability, and excellent aesthetics (stand-up, texture, dispersion).

Additional dentifrice formulations were formulated based on the inventive abrasive slurries as follows. A portion of Silica Wet Cake 4 was fluidized with sorbitol as described in Table 5D below, and using general protocol described above in the examples, and thereafter dentifrice was formulated with this fluidized silica wet cake as described in Table 5E below. Properties of this dentifrice formulation are given in Table 5F below. Also silica wet cake (WC2) was fluidized with humectant and thereto was added separately PCC wet cake or dry dicalcium phosphate as indicated in Table 5D. These fluidized slurries were incorporated into the dentifrice formula of Table 5E and these toothpaste properties are summarized in Table 5F.

TABLE 5D

Toothpaste Formula A'
Slurry Component Make-up

| | Silica blend | | Silica/PCC | | Silica/DCP | |
|---|---|---|---|---|---|---|
| Abrasive Slurry No. | 15 | 16 | 17 | 18 | 19 | 20 |
| Deionized Water, g | — | — | 81 | — | 205 | — |
| Sorbitol, g | 100.5 | — | 269 | — | — | — |
| Glycerin, g | — | — | — | — | 183.5 | — |
| WC1 | 331.6 | — | — | — | — | — |
| WC2 | 70.5 | — | 70.5 | — | 168.9 | — |
| WC1 (dry & milled) | — | 400 | — | — | — | — |
| WC2 (dry & milled) | — | 100 | — | 100 | — | 9 |

TABLE 5D-continued

Toothpaste Formula A'
Slurry Component Make-up

| Abrasive Slurry No. | Silica blend 15 | 16 | Silica/PCC 17 | 18 | Silica/DCP 19 | 20 |
|---|---|---|---|---|---|---|
| PCC press cake, g | — | — | 198.5 | — | — | — |
| PCC flash dried, g | — | — | — | 400 | — | — |
| Dicalcium phosphate dihydrate, g | — | — | — | — | 360 | 36 |
| Total | 502.6 | 500 | 619 | 500 | 917.4 | 45 |
| % 325 Residue | 1.5 | | 1.48 | | 0.61 | |
| Viscosity, cP | 2320 | | — | | — | |

*the drying and milling procedure was the same as that described in footnote "*" of Table 5a.

TABLE 5E

Toothpaste Formulation A

| Toothpaste Formula # | 10 | 1I | 12 | 13 | 14 | 15 |
|---|---|---|---|---|---|---|
| Glycerin 99.5%, g | 11.6 | 11.6 | 11.6 | 11.6 | 3.65 | 22 |
| CMC-7MF, g | 1.4 | 1.4 | 1.4 | 1.4 | 1.2 | 1.2 |
| Sorbitol, 70%, g | 28.21 | 38.257 | 11.36 | 38.257 | 0 | 0 |
| Deionized water, g | 4.79 | 25 | 10 | 25 | 0 | 28.39 |
| Sodium Fluoride, g | 0.243 | 0.243 | 0.243 | 0.243 | 0 | 0 |
| Sodium monofluorophosphate, g | — | — | — | — | 0.76 | 0.76 |
| Trisodium phosphate | — | — | — | — | 0.5 | 0.5 |
| Sodium Saccharin, g | 0.3 | 0.3 | 0.3 | 0.3 | 0.2 | 0.2 |
| Sodium Benzoate, g | 0.5 | 0.5 | 0.5 | 0.5 | 0 | 0 |
| $TiO_2$, g | 0.5 | 0.5 | 0.5 | 0.5 | 0 | 0 |
| Abrasive Slurry No. | | | | | | |
| 15, g | 50.26 | — | — | — | — | — |
| 16, g | — | 20 | — | — | — | — |
| 17, g | — | — | 61.9 | — | — | — |
| 18, g | — | — | — | 20 | — | — |
| 19, g | — | — | — | — | 91.74 | — |
| 20, g | — | — | — | — | — | 9 |
| Dicalcium phosphate dihydrate, g | — | — | — | — | — | 36 |
| Sodium lauryl sulfate, g | 1.2 | 1.2 | 1.2 | 1.2 | 1.3 | 1.3 |
| Flavor, g | 1 | 1 | 1 | 1 | 0.65 | 0.65 |
| Total | 100.00 | 100.00 | 100.00 | 100.00 | 100.00 | 100.00 |

TABLE 5F

Toothpaste Formulation A Performance Data

| Toothpaste Formula No. | 10 | 11 | 12 | 13 | 14 | 15 |
|---|---|---|---|---|---|---|
| Initial Viscosity, cP | 500,000 | 270,000 | 270,000 | 140,000 | 1,200,000 | 400,000 |
| 1 Wk Viscosity, cP | 490,000 | 220,000 | 340,000 | 340,000 | 1,530,000 | 480,000 |
| 3 Wk Viscosity, cP | 680,000 | 400,000 | 400,000 | 170,000 | 1,600,000 | 410,000 |
| 6 Wk Viscosity, cP | 640,000 | 340,000 | 380,000 | 120,000 | 1,290,000 | 520,000 |
| 25% pH | 6.56 | 7.2 | 9.45 | 9.66 | 7.04 | 7.05 |
| Gravity Specific | 1.301 | 1.292 | 1.301 | 1.275 | 1.454 | 1.521 |
| % F/A 3 Wk 80 F. | 100 | 87 | 13 | 17 | 92 | 92 |
| L value | 90.8 | 91.4 | 92.4 | 90.6 | — | — |
| $a_L$ | -2.2 | -1.9 | -1.8 | -1.5 | — | — |
| $b_L$ | 3.6 | 3.1 | 4.6 | 4 | — | — |

All dentifrices made with the inventive abrasive slurries, even in combination with other abrasive exhibited good viscosity and aesthetic properties.

Example 5

Silica wet cake 3 was fluidized as described in Table 6A, then wet milled and screened prior to incorporation into a toothpaste formulation. To do this, the fluidized wet cake as described above was introduced into a Spex mill model 8000 or 76140 to reduce the median particle size of the silica/humectant slurry. To do this, 100 g of slurry and five 1.2 cm ceramic wet pebble milling media were placed in an appropriate container and milled for 25 minutes, and then the milling media was removed. Thereafter, the wet milled slurry was mesh screened in the same manner as described in Example 4. The wet milled and screened slurry was formulated into a low water clear gel dentifrice formulation described in Table 6B. Properties of this dentifrice are given in Table 6C.

For comparison, a portion of silica wet cake 3, which was dried and milled in the same way as wet cake used in making abrasive slurry No. 13 above, was also incorporated into a dentifrice formulation.

TABLE 6A

Toothpaste Formula B
Slurry Component Make-up

| Abrasive Slurry No. | 21 | 22 |
|---|---|---|
| Deionized Water, g | 80.6 | — |
| Sorbitol, 70%, g | 113.6 | — |
| WC3 | 373.8 | — |
| WC3 (dry & milled) | — | 10 |
| Total | 568 | 10 |
| % 325 Residue | 0 | |
| Viscosity, cP | 960 | |
| Screened | yes | |
| Spex Milled | yes | |

TABLE 6B

Toothpaste Formula B

| Toothpaste formulation No. | 16 | 17 |
|---|---|---|
| Sorbitol, 70%, ,g | 52.32 | 58 |
| Carbowax 600 , g | 5 | 5 |
| CMC-7MXF, g | 0.4 | 0.4 |
| Sodium Benzoate, g | 0.5 | 0.5 |
| Sodium Saccharin, g | 0.2 | 0.2 |
| Sodium Monofluorophosphate, g | 1.11 | 1.11 |
| Deionized water, g | 0 | 12.715 |
| Zeodent ® 165 silica thickener** | 8.5 | 8.5 |
| Abrasive Slurry No. 21 | 28.4 | — |
| Abrasive Slurry No. 22 | — | 10 |
| 1% FD&C green No. 3, g | 0.2 | 0.2 |
| Sodium lauryl sulfate, g | 1.875 | 1.875 |
| Flavor, g | 1.5 | 1.5 |
| Total | 100 | 100 |

*Carbowax 600 is available from Union Carbide Corporation, Danbury, CT.
**Zeodent ® 165 silica thickener is available from J. M. Huber Corporation.

TABLE 6C

Toothpaste Formulation B Performance Data

| Toothpaste formulation No. | 16 | 17 |
|---|---|---|
| Initial Viscosity, cP | 220,000 | 290,000 |
| 1 Wk Viscosity, cP | 270,000 | 360,000 |
| 3 Wk Viscosity, cP | 290,000 | 500,000 |
| 6 Wk Viscosity, cP | 410,000 | 480,000 |
| 25% pH | 6.45 | 6.61 |
| Specific Gravity | 1.313 | 1.313 |
| Haze Rating (140 F.) | 94 | 95 |

As can be seen from data in the above Table 6C, the inventive silica abrasive slurry made a gel toothpaste with excellent viscosity, and haze comparable to that of the toothpaste made with the corresponding dry abrasive.

The various silica, silica slurry, and toothpaste (dentifrice) properties described herein were measured as follows, unless indicated otherwise.

The precipitated silicas have a median particle size measured using a Microtrac II apparatus, made by Leeds and Northrup.

The Brass Einlehner (BE) Abrasion test used to measure the hardness of the precipitated silicas reported in this application involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams brass lost from the Fourdrinier wire screen per 100,000 revolutions. The result, measured in units of mg loss, can be characterized as the 10% brass Einlehner (BE) abrasion value.

The oil absorption values are measured using the rubout method. This method is based on a principle of mixing linseed oil with a silica by rubbing with a spatula on a smooth surface until a stiff putty-like paste is formed. By measuring the quantity of oil required to have a paste mixture which will curl when spread out, one can calculate the oil absorption value of the silica—the value which represents the volume of oil required per unit weight of silica to saturate the silica sorptive capacity. Calculation of the oil absorption value was done as follows:

$$\text{Oil absorption} = \frac{cc \text{ oil absorbed}}{\text{weight of silica, grams}} \times 100$$

$$= cc \text{ oil}/100 \text{ gram silica}$$

To determine toothpaste fluoride availability (F/A), a soluble fluoride determination method is used. Toothpaste compositions are stored at a specified temperatures for a specified length of time in a laminated tube. Thereafter, 10 grams of the toothpaste composition is placed in a 10 ml beaker and 30 grams of distilled water is added. The mixture is stirred to form a uniformly dispersed toothpaste slurry. The slurry is subsequently centrifuged for 10 minutes at 15,000 rpm or until the supernatant is clear. Then 10 ml of the supernatant and 10 ml of pH 8 buffer (0.2 $\underline{N}$ EDTA/0.2 $\underline{N}$ THAM (2-amino-2-hydroxymethyl-1,3-propanediol), previously adjusted to pH=8.0 with NaOH) is pipetted into a plastic vial., a magnetic stir bar added and gentle stirring is initiated. The fluoride ion concentration is determined by direct potentiometry with an Orion fluoride electrode (Model 95–09) utilizing 1000 and 100 ppm F standards to set instrument calibration. Fluoride Availability (% F/A) is the percent fluoride determined in the supernatant versus that originally added to the toothpaste, based on the toothpaste abrasive loading level.

The toothpaste (dentifrice) viscosity is measured utilizing a Brookfield Viscometer Model RVT equipped with a Helipath T-E spindle and set to 5 rpm by measuring the viscosity of the toothpaste at 25° C. at three different levels as the spindle descends through the toothpaste test sample and averaging the results. Brookfield viscosity is expressed in centipoise (cP).

Toothpaste haze and color (L, $a_L$, $b_L$) is measured utilizing a Gardner XL-835 Colorimeter by measuring light transmission. Specifically, two 38×75×1 mm microscope slides are placed on a flat surface. A plexiglass spacer (38×75×3 mm thick with a 24×47 mm cut-out open space) is placed on top of one of the slides. Toothpaste gel is squeezed into the open area of the plexiglass spacer and the second microscope slide is placed on top of the spacer with enough pressure (by hand) to eliminate excess air and toothpaste. The slide is placed on the calorimeter transmission light beam opening (haze) and the back port (color) and three readings are taken at different specimen spacer locations and averaged. The specimen should have no visible air bubbles.

The Radioactive Dentin Abrasion (RDA) values of the precipitated silica compositions used in this invention are determined according to the method set forth by Hefferen, Journal of Dental Res., July–August 1976, 55 (4), pp. 563–573, and described in Wason U.S. Pat. Nos. 4,340,583, 4,420,312 and 4,421,527, which publications and patents are incorporated herein by reference.

The cleaning and abrasiveness properties of dentifrice compositions are typically expressed in terms of Pellicle Cleaning Ratios ("PCR") and Radioactive Dentin Abrasion ("RDA") values, respectively. The PCR test measures the ability of a dentifrice composition to remove pellicle film from a tooth under fixed brushing conditions. The PCR test is described in "In Vitro Removal of Stain With Dentifrice" G. K. Stookey, et al., J. Dental Res., 61, 1236–9, 1982. The RDA test measures the abrasiveness of dentifrice compositions by measuring the amount of radio-labeled dentin removed from a tooth under fixed brushing conditions. Both PCR and RDA results vary depending upon the nature and concentration of the components of the dentifrice composition. PCR and RDA values are unitless.

The surface area of the precipitated silica reported herein is determined the BET nitrogen adsorption method of Brunaur et al., J. Am. Chem. Soc., 60, 309 (1938).

To measure TAPPI brightness, fine powder materials, viz., silica particles here, are pressed into a smooth surfaced pellet are evaluated using a Technidyne Brightmeter S-5BC. This instrument has a dual beam optical system where the sample is illuminated at an angle of 45°, and the reflected light viewed at 0°. It conforms to TAPPI test methods T452 and T646, and ASTM Standard D985. Powdered materials are pressed to about a 1 cm thick pellet with enough pressure to provide a pellet surface that is smooth and flat and without loose particles or gloss.

The total pore volume (Hg) is measured by mercury porosimetry using a Micromeritics Autopore II 9220 apparatus. The pore diameters can be calculated by the Washburn equation employing a contact angle Theta ($\theta$) equal to 130° and a surface tension gamma equal to 484 dynes/cm. This instrument measures the void volume and pore size distribution of various materials. Mercury is forced into the voids as a function of pressure and the volume of the mercury intruded per gram of sample is calculated at each pressure setting. Total pore volume expressed herein represents the cumulative volume of mercury intruded at pressures from vacuum to 60,000 psi. Increments in volume ($cm^3/g$) at each pressure setting are plotted against the pore radius or diameter corresponding to the pressure setting increments. The peak in the intruded volume versus pore radius or diameter curve corresponds to the mode in the pore size distribution and identifies the most common pore size in the sample. Specifically, sample size is adjusted to achieve a stem volume of 30–50% in a powder penetrometer with a 5 ml bulb and a stem volume of about 1.1 ml. Samples are evacuated to a pressure of 50 $\mu$m of Hg and held for 5 minutes. Mercury fills the pores from 1.5 to 60,000 psi with a 10 second equilibrium time at each of approximately 150 data collection points.

CTAB external surface area of silica is determined by absorption of CTAB (cetyltrimethylammonium bromide) on the silica surface, the excess separated by centrifugation and determined by titration with sodium lauryl sulfate using a surfactant electrode. The external surface of the silica is determined from the quantity of CTAB adsorbed (analysis of CTAB before and after adsorption). Specifically, about 0.5 g of silica is placed in a 250-ml beaker with 100.00 ml CTAB solution (5.5 g/L), mixed on an electric stir plate for 1 hour, then centrifuged for 30 minutes at 10,000 rpm. One ml of 10% Triton X-100 is added to 5 ml of the clear supernatant in a 100-ml beaker. The pH is adjusted to 3.0–3.5 with 0.1 $\underline{N}$ HCI and the specimen is titrated with 0.0100 M sodium lauryl sulfate using a surfactant electrode (Brinkmann SUR1501-DL) to determine the endpoint.

The % 325 mesh is measured utilizing a U.S. Standard Sieve No. 325, with 44 micron or 0.0017 inch openings (stainless steel wire cloth) by weighing a 10.0 gram sample to the nearest 0.1 gram into the cup of the 1 quart Hamilton mixer Model No. 30, adding approximately 170 ml of distilled or deionized water and stirring the slurry for at least 7 min. Transfer the mixture onto the 325 mesh screen; wash out the cup and add washings onto the screen. Adjust water spray to 20 psi and spray directly on screen for two minutes. (Spray head should be held about four to six inches above the screen cloth. Wash the residue to one side of the screen and transfer by washing into an evaporating dish using distilled or deionizedwater from a washing bottle. Let stand for two to three minutes and decant the clear water. Dry (convection oven @ 150° C. or under infrared oven for approx. 15 min.) cool and weigh residue on analytical balance.

Moisture is the measured sample weight loss at 105° C. for 2 hours. The pH values of the reaction mixtures (5 weight % slurry) encountered in the present invention can be monitored by any conventional pH sensitive electrode.

It will be understood that various changes in the details, materials, and arrangements of the parts which have been described and illustrated herein in order to explain the nature of this invention may be made by those skilled in the art without departing from the principles and scope of the invention as expressed in the following claims.

What is claimed is:

1. A dentifrice composition, comprising combining an abrasive slurry, binder, and optionally a source of water soluble fluoride, wherein the abrasive slurry is prepared by dispersing undried water insoluble synthetic abrasive particles with a liquid medium comprising humectant, whereby the synthetic abrasive particles are suspended in the slurry.

2. The dentifrice composition according to claim 1, wherein the water-insoluble abrasive particles are selected from the group consisting of precipitated silica, silica gel, dicalcium phosphate, calcium pyrophosphate and precipitated calcium carbonate.

3. The dentifrice composition according to claim 1, wherein the water-insoluble abrasive particles comprise precipitated silica.

4. The dentifrice composition according to claim 3, wherein the precipitated silica particles have a median particle size of about 1 to about 15 microns ($\mu$m).

5. The dentifrice composition according to claim 3, wherein the precipitated silica has a brass Einlehner value of about 0.5 to about 30, a PCR of about 50 to about 200, an RDA value of about 30 to about 200, and a linseed oil absorption value from about 40 to about 200 cc/100 g.

6. The dentifrice composition according to claim 1, wherein the humectant comprises a polyol.

7. A dentifrice composition, comprising: binder, flavoring agent, a suspension of synthetic abrasive particles, and optionally a source of water soluble fluoride, wherein the suspension of synthetic abrasive particles is a product of the steps comprising providing a reaction system including a reaction container and a high shear mixing means arranged for treating reaction mixture contents of the reaction container; introducing into the reaction system, as the reaction mixture contents, alkali silicate and acid into the reaction system with intermixing thereof to form precipitated silica; withdrawing approximately 5 vol. % to approximately 50 vol. % per minute portion of the total volume of the reaction mixture contents of the reaction container and conducting the withdrawn portion through the high shear mixing means and re-introducing such conducted volume of reaction mixture contents back into the reaction mixture in the reaction container after passage through the high shear mixing means; separating the precipitated silica from the reaction mixture with a filter to provide a filter cake; washing the filter cake; and fluidizing the precipitated silica in the filter cake by combining humectant with the precipitated silica to provide the suspension of synthetic abrasive particles.

8. A method for preparing a dentifrice composition, comprising the steps of:

providing an abrasive slurry comprising undried water insoluble synthetic abrasive particles in combination with a liquid medium comprising humectant, whereby the synthetic abrasive particles are suspended in the slurry; and mixing said abrasive slurry with a flavoring agent.

9. The method of claim 8, wherein the abrasive slurry comprises a water content less than about 50 weight percent.

10. The method of claim 8, wherein said water-insoluble abrasive particles being derived from a precipitation reaction without being dried and dry comminuted before being suspended in said liquid medium.

11. A method for preparing a dentifrice composition, comprising the steps of:

providing a reaction system including a reaction container and a high shear mixing means arranged for treating reaction mixture contents of the reaction container;

introducing into the reaction system, as the reaction mixture contents, alkali silicate and acid into the reaction system with inter-mixing thereof to form precipitated silica;

withdrawing approximately 5 vol. % to approximately 50 vol. % per minute portion of the total volume of the reaction mixture contents of the reaction container and conducting the withdrawn portion through the high shear mixing means and re-introducing such conducted volume of reaction mixture contents back into the reaction mixture in the reaction container after passage through the high shear mixing means;

separating the precipitated silica from the reaction mixture with a filter to provide a filter cake;

washing the filter cake;

fluidizing the precipitated silica in the filter cake by combining humectant with the precipitated silica, to provide a suspension of abrasive particles containing humectant; and combining said suspension of abrasive particles with a flavoring agent.

12. A method according to claim 11, wherein said reaction system includes a recirculation loop for withdrawal of the portion of the flowable reaction mixture contents in the reaction container from a first location thereof and re-introduction of said portion back into the reaction container at a second location thereof, wherein the recirculation loop includes pumping means and an in-line high shear mixer.

13. The method according to claim 12, wherein said acid is introduced at the high shear in-line mixer into the portion of the reaction mixture contents passing through the recirculation loop.

14. The method according to claim 11, wherein the high shear mixer comprises a rotor/stator mixer.

15. The method according to claim 11, wherein the abrasive composition comprises a plurality of precipitated silica particles having a median particle size of about 1 micron to about 30 micron.

16. The method according to claim 11, wherein the abrasive composition comprises a plurality of precipitated silica particles having a median particle size of about 3 micron to about 15 micron.

17. The method according to claim 12, wherein the withdrawing step comprises passing approximately 8 vol. % to 22 vol. % per minute of the volume of the contents of the reaction container through the recirculation loop.

18. The method according to claim 11, wherein the humectant is present in the suspension of abrasive particles in an amount of about 3 to about 80 wt % humectant.

19. The method according to claim 11, further comprising adding a preservative to the suspension of abrasive particles with mixing.

20. The method according to claim 11, wherein the preservative is selected from the group consisting of sodium benzoate, tetrasodium pyrophosphate, propyl-p-hydroxy-benzoate, and methyl-p-hydroxy-benzoate (methyl paraben).

21. The method according to claim 11, further comprising continuously maintaining the aqueous suspension of abrasive particles at a total liquid content of at least 20 wt % from after the withdrawing step up until initiating said combining step.

22. The method according to claim 11, wherein said combining step further comprises adding at least one of water, additional humectant, a source of water soluble fluoride ions, binder, flavoring agent, coloring agent, whitening agent, preservative, tarter control compound, foaming agent, and/or anti-microbial agent.

23. The method according to claim 11, further comprising the step of wet milling the suspension of abrasive particles after introducing the humectant and before the combining step.

24. The method according to claim 11, further comprising the step of screening the suspension of abrasive particles after introducing the humectant and before the combining step.

25. The product of the method of claim 11.

* * * * *